US009662119B2

(12) United States Patent
Ortega et al.

(10) Patent No.: US 9,662,119 B2
(45) Date of Patent: May 30, 2017

(54) SHAPE-MEMORY POLYMER FOAM DEVICE FOR TREATING ANEURYSMS

(71) Applicants: Lawrence Livermore National Security, LLC, Livermore, CA (US); The Texas A&M University System, College Station, TX (US); Jonathan Hartman, Sacramento, CA (US)

(72) Inventors: Jason M. Ortega, Pacifica, CA (US); William J. Benett, Livermore, CA (US); Ward Small, Livermore, CA (US); Thomas S. Wilson, San Leandro, CA (US); Duncan J Maitland, College Station, TX (US); Jonathan Hartman, Sacramento, CA (US)

(73) Assignees: Lawrence Livermore National Security, LLC, Livermore, CA (US); The Texas A&M University System, College Station, TX (US)

( * ) Notice: Subject to any disclaimer, the term of this patent is extended or adjusted under 35 U.S.C. 154(b) by 711 days.

(21) Appl. No.: 13/798,740

(22) Filed: Mar. 13, 2013

(65) Prior Publication Data
US 2014/0277057 A1 Sep. 18, 2014

(51) Int. Cl.
*A61M 29/00* (2006.01)
*A61B 17/12* (2006.01)
*A61B 17/00* (2006.01)

(52) U.S. Cl.
CPC .. *A61B 17/12113* (2013.01); *A61B 17/12022* (2013.01); *A61B 17/12031* (2013.01); *A61B 17/12181* (2013.01); *A61B 2017/0061* (2013.01); *A61B 2017/00871* (2013.01); *A61B 2017/12077* (2013.01)

(58) Field of Classification Search
CPC .......... A61B 17/12113; A61B 17/1214; A61B 17/12172; A61B 17/1219; A61B 2017/00867; A61B 2017/12113
See application file for complete search history.

(56) References Cited

U.S. PATENT DOCUMENTS

| 8,133,256 | B2 | 3/2012 | Wilson et al. | |
|---|---|---|---|---|
| 2002/0143349 | A1* | 10/2002 | Gifford et al. | 606/157 |
| 2003/0187473 | A1* | 10/2003 | Berenstein | A61B 17/12022 606/200 |
| 2004/0143288 | A1* | 7/2004 | Searle | 606/200 |
| 2005/0182428 | A1 | 8/2005 | Bearinger et al. | |

(Continued)

FOREIGN PATENT DOCUMENTS

| WO | 03082128 | 10/2003 |
|---|---|---|
| WO | 2006111801 | 10/2006 |
| WO | 2007006139 | 6/2011 |

*Primary Examiner* — Julie A Szpira
(74) *Attorney, Agent, or Firm* — Eddie E. Scott

(57) ABSTRACT

A system for treating an aneurysm in a blood vessel or vein, wherein the aneurysm has a dome, an interior, and a neck. The system includes a shape memory polymer foam in the interior of the aneurysm between the dome and the neck. The shape memory polymer foam has pores that include a first multiplicity of pores having a first pore size and a second multiplicity of pores having a second pore size. The second pore size is larger than said first pore size. The first multiplicity of pores are located in the neck of the aneurysm. The second multiplicity of pores are located in the dome of the aneurysm.

13 Claims, 14 Drawing Sheets

(56) References Cited

U.S. PATENT DOCUMENTS

| | | | |
|---|---|---|---|
| 2006/0052816 A1* | 3/2006 | Bates et al. | 606/200 |
| 2007/0135907 A1* | 6/2007 | Wilson | A61B 17/12022 623/1.44 |
| 2010/0094335 A1* | 4/2010 | Gerberding et al. | 606/213 |
| 2011/0144686 A1 | 6/2011 | Wilson et al. | |
| 2012/0253369 A1* | 10/2012 | Morsi | 606/158 |
| 2014/0135812 A1* | 5/2014 | Divino et al. | 606/194 |

* cited by examiner

SHAPE-MEMORY POLYMER FOAM DEVICE FOR TREATING ANEURYSMS

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to treating aneurysms and more particularly to a shape memory polymer foam device for treating aneurysms.

State of Technology

U.S. Pat. No. 8,133,256 for shape memory polymer foams for endovascular therapies provides the state of technology information quoted below.

"In the general application, a vascular anomaly is treated using the device with the intent of stabilizing the anomaly from further expansion and possible rupture. The device is delivered endovascularly to the site for therapy via a catheter. The catheter may be previously placed using a conventional guidewire or the device may be installed using the guidewire. Once the catheter is placed near the therapeutic site, the device is placed into the anomaly with the guidewire and guided visually by radiology. The device is then held in place and the foam is actuated to expand, filling the anomaly. Once expanded, the foam will stay in place on its own or an additional aid will be used to hold it in place; for example, a diaphragm for the aneurysm or a stent for the AVM. The foam is released from the guidewire or catheter via the expansion process or following actuation by known techniques. The guidewire and/or catheter is then retracted and the therapy is completed. Should there be a misplacement of the foam, retrieval is possible using another shape-memory polymer device or other conventional techniques."

"Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while is an elastomeric state and that shape is fixed in one of several ways including cooling the polymer below a crystalline, liquid crystalline, or glass transition temperature; by inducing additional covalent or ionic crosslinking, etc."

"While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower Tg) or physical restraints (physical or chemical crosslinks). Actuation then occurs for the recovery to the primary shape by removing that restraint, e.g., heating the polymer above its glass transition or melting temperature, removing ionic or covalent crosslinks, etc. Other types of polymers which undergo shape memory behavior due to photon induced conformational transformations, conformational changes (e.g., rod-coil transition) due to changes in chemical environment (pH, ionic strength, etc.), or structural changes due to imposed fields (e.g., electric, magnetic, . . . ) may also be used. Both shape memory alloys (SMAs) and shape memory polymers (SMPs) can be used for the shape memory material of the present invention."

"A shape memory material therapeutic device has advantages over existing therapeutic devices of being able to be moved more easily through the catheter to the point of placement, A shape memory material therapeutic can be placed more precisely within the geometry of the vascular disorder, and there is a higher degree of control over the expansion process while the device was being held in the desired position. A shape memory material therapeutic can be controllably expanded while being held in precise placement. A shape memory material therapeutic expands to its secondary shape within a few seconds, which is much faster than current expandable hydrogel based devices. The modulus of the devices can be accurately controlled so that expansion forces are low and no damage is done to areas of the vascular lumen.

The shape memory material device is expandable from 100% to 10000% by volume. The shape memory material device is actuated by one of several means including electromagnetic energy delivered optically. The shape memory material device is used to occlude part or all of a lumen, aneurysm, artiovascular malformation, or other physical anomaly."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a shape memory polymer foam system for treating aneurysms. In one embodiment the present invention provides an apparatus for treating an aneurysm in a blood vessel or vein, wherein the aneurysm has a dome, an interior, and a neck. The apparatus provides a shape memory polymer foam in the interior of the aneurysm between the dome and the neck. The shape memory polymer foam has pores that include a first multiplicity of pores having a first pore size and a second multiplicity of pores having a second pore size. The second pore size is larger than said first pore size. The first multiplicity of pores are located in the neck of the aneurysm. The second multiplicity of pores are located in the dome of the aneurysm. This provides a shape memory polymer foam system with foam porosity, permeability, and shape to stagnate the blood flow within the aneurysm and to promote thrombus and collagen formation throughout the SMP foam.

The present invention provides a shape memory polymer foam system with a gradation of foam pore size in a continuous fashion from one end of the single piece of foam to the other end. This places the least permeable portion of foam nearest the parent artery, where the blood flow has the highest speed. Consequently, the small pore sizes near the aneurysm neck rapidly decelerate the flow as it enters the aneurysm. Near the aneurysm fundus, where the blood flow has a much smaller speed, the pore sizes are larger since it is not necessary to further decelerate the flow in this region.

The present invention has two major advantages. First, it allows for smaller treatment devices since only the necessary amount of foam material required for healing is incorporated into the device. The result is a compact design that can easily reach small intracranial arteries where aneurysms typically form. Second, the present invention preserves essential blood flow to vessels that often line the aneurysm wall.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
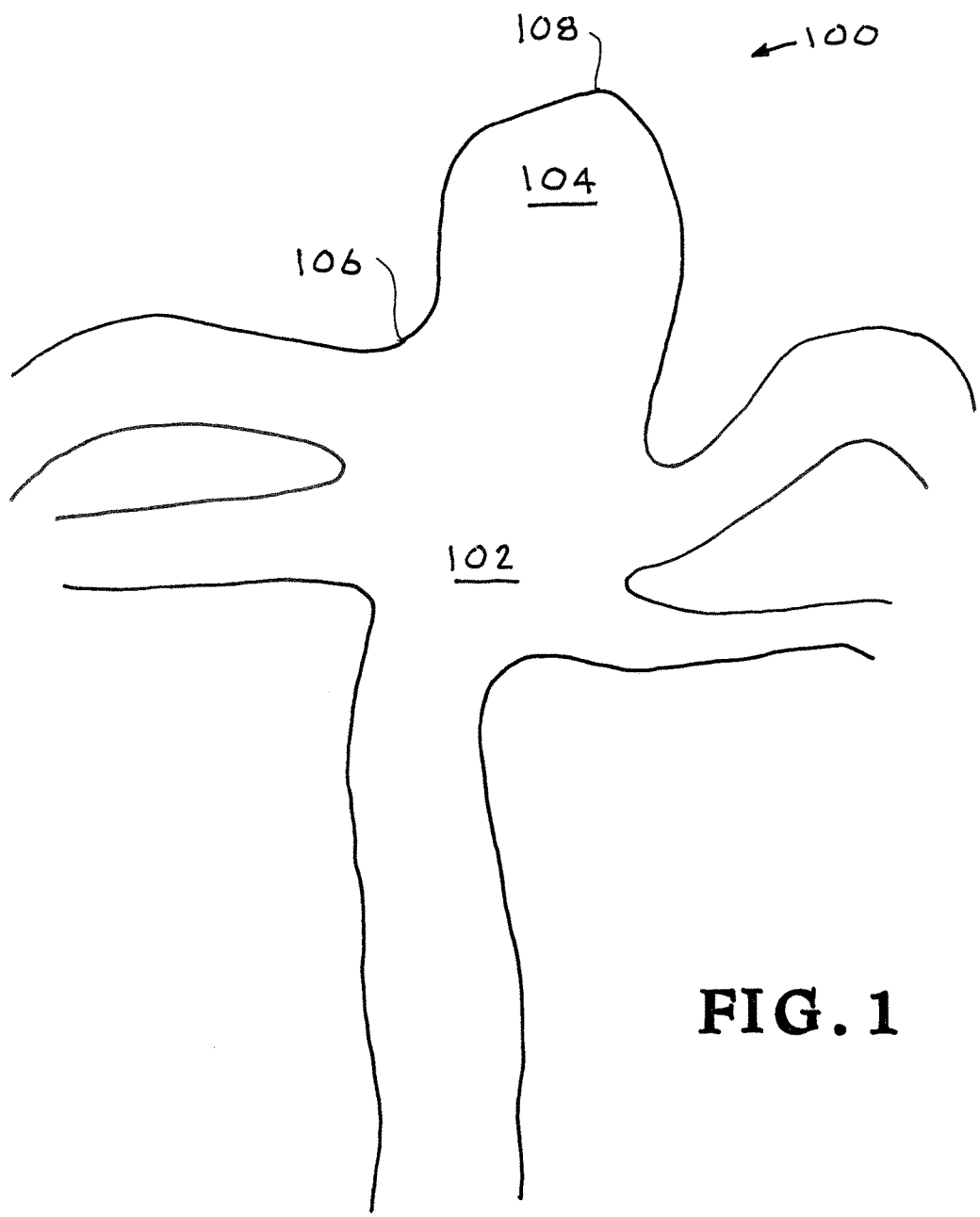
FIG. 1 is an illustration showing a blood vessel and artery system with an aneurysm.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides systems for treating aneurysms. This invention has particular advantage for treating cranial aneurysms and will be described by various embodiments relating to cranial aneurysms; however it is to be understood that the scope of the invention is not intended to be limited to the particular embodiments and forms disclosed and the invention covers all modifications, equivalents, and alternatives falling within the spirit and scope of the invention as defined by the claims.

A cranial aneurysm is a condition that is often asymptomatic until the time of rupture. Subarachnoid hemorrhage associated with aneurysmal rupture is a potentially lethal event with a mortality rate as high as 50 percent. Many patients who survive the initial hemorrhage have permanent disability. A cranial aneurysm, also called cerebral or brain aneurysm, is a disorder in the veins or vascular system of the brain. Cerebral veins or arteries become weak and cause the blood vessels to balloon or dilate. Aneurysms are often found in the Circle of Willis, which is a group of arteries found at the base of the brain. The majority, about 85%, occur in the anterior part of this area. They often happen in the parts of cerebrovascular system that provide blood to the anterior and middle sections of the brain, usually with the internal carotid arteries and their main branches. There are different kinds of aneurysms based on size and shape. Those less than 15 mm are considered small. A size of 15 to 25 mm means the aneurysms are large while those found over 50 mm are considered super giants. The most common shape of aneurysms is saccular; this means it has some saccular outpouching. Some of these saccular aneurysms also have a stem or neck; these are called berry aneurysms. Those without stems are called fusiform aneurysms. Congenital defects or head trauma can lead to aneurysms. The more common cause is high blood pressure and atherosclerosis or the buildup of fatty deposits in the arteries. This is a greater cause for concern in the midst of the obesity problem in developed countries. This disorder does not adhere to any age range, but occurs more often in adults. It also favors women with a ratio of 3 to 2.

The present invention provides systems for treating these intracranial aneurysms through the endovascular delivery of a shape memory polymer foam (SMP) device. The systems function by producing flow conditions within the post-treatment aneurysm that optimize the body's healing response to the treatment procedure. This invention includes systems for customizing the SMP foam structure of the device to obtain flow conditions within the post-treatment aneurysm that optimize the body's healing response to the treatment procedure. In various embodiments the present invention provides systems for designing the SMP foam porosity, permeability, and shape to stagnate the blood flow within the aneurysm and to promote thrombus and collagen formation throughout the SMP foam.

The system of the present invention provides a number of advantages. For example, it allows for smaller treatment devices since only the necessary amount of SMP foam material required for healing is incorporated into the device. The result is a compact design that can easily reach small intracranial arteries where aneurysms typically form. Also, the system of the present invention preserves essential blood flow to vessels that often line the aneurysm wall by including channels that deliver blood from the parent artery to these vessels. Such transport will not only maintain the health of tissue downstream of these vessels, but will also provide a robust means of promoting the body's healing response to the treatment procedure. The current FDA-approved technique of treating aneurysms with detachable metal coils and/or an endoluminal stent do not provide this advantage since the coils randomly fill the aneurysm, thereby occluding these vessels.

The present invention is further described and illustrated by a number of examples of systems constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims.

Referring now to the drawings and in particular to FIG. 1, an illustration shows a blood vessel and artery system with an aneurysm. The illustration is designated generally by the reference numeral 100. The illustration 100 represents cerebral arteries and blood vessels 102. An aneurysm 104 is shown as a bulging or ballooning in the wall. It is caused when a portion of the wall weakens. As the aneurysm 104 expands, there is an increased likelihood that the aneurysm will burst. The aneurysm 104 is shown with a dome 108 and a neck 106.

Example 1

Single Piece of SMP Foam

Figure 2:
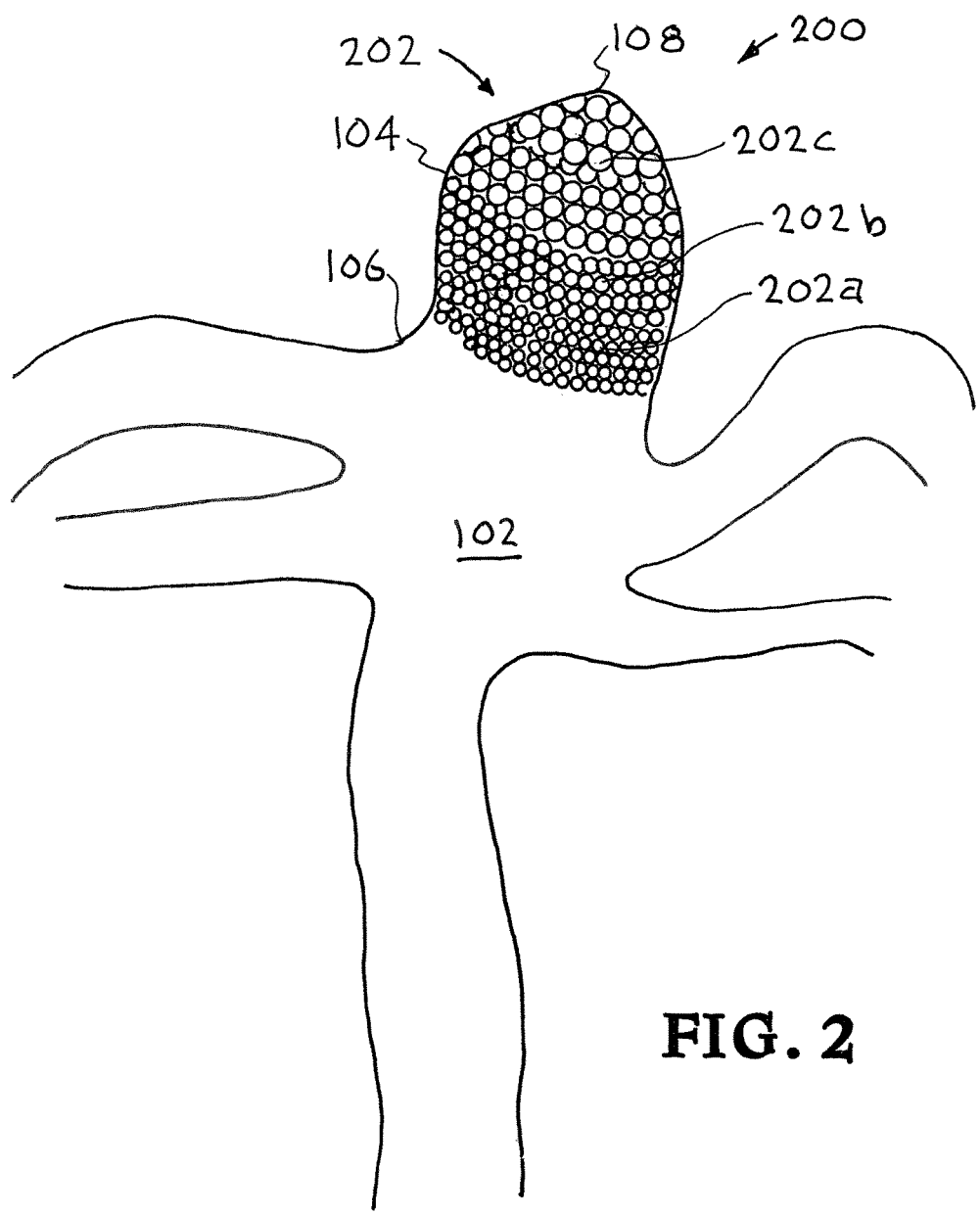
FIG. 2 is the illustration the blood vessel and artery system with an aneurysm shown in FIG. 1 wherein a single piece of foam fills the aneurysm.

Referring now to FIG. 2, an illustration shows the blood vessel and artery system and the aneurysm that were illustrated in FIG. 1. The illustration is designated generally by the reference numeral 200. The illustration 200 shows the cerebral arteries and blood vessels 102 and the aneurysm 104. The aneurysm 104 is shown with a dome 108 and a neck 106. The aneurysm 104 is shown with a single piece of SMP foam 202 in the aneurysm 104.

As illustrated in FIG. 2, the single piece of SMP foam 202 fills the aneurysm 104. The single piece of SMP foam 202 has a gradation of SMP foam pore size 202a, 202b, and 202c in a continuous fashion from one end of the single piece of SMP foam to the other end. This places the least permeable portion 202a of the SMP foam nearest the parent artery, where the blood flow has the highest speed. Consequently, the small pore sizes 202a near the aneurysm neck rapidly decelerate the flow as it enters the aneurysm. Near the aneurysm fundus, where the blood flow has a much smaller speed, the pore sizes 202c are larger since it is not necessary to further decelerate the flow in this region. Through this gradation of pore sizes 202a, 202b, and 202c, the total amount of polymer material comprising the device can be reduced. In general, the cranial aneurysm 104 is treated using a device for stabilizing the aneurysm from further expansion and possible rupture. The device is delivered endovascularly to the site for treatment via a catheter. The catheter may be previously placed using a conventional guidewire or the device may be installed using a guidewire. Once the catheter is placed near the treatment site, the device is placed into the anomaly with the guidewire and guided visually by radiology.

The device is then held in place and the SMP foam is actuated to expand, filling the aneurysm. Once expanded, the SMP foam will stay in place on its own or an additional aid can be used to hold it in place. The SMP foam is released from the guidewire or catheter via the expansion process or following actuation by known techniques. The guidewire and/or catheter is then retracted and the treatment is completed.

Example 2

Separate Pieces of SMP Foam

Figure 3:
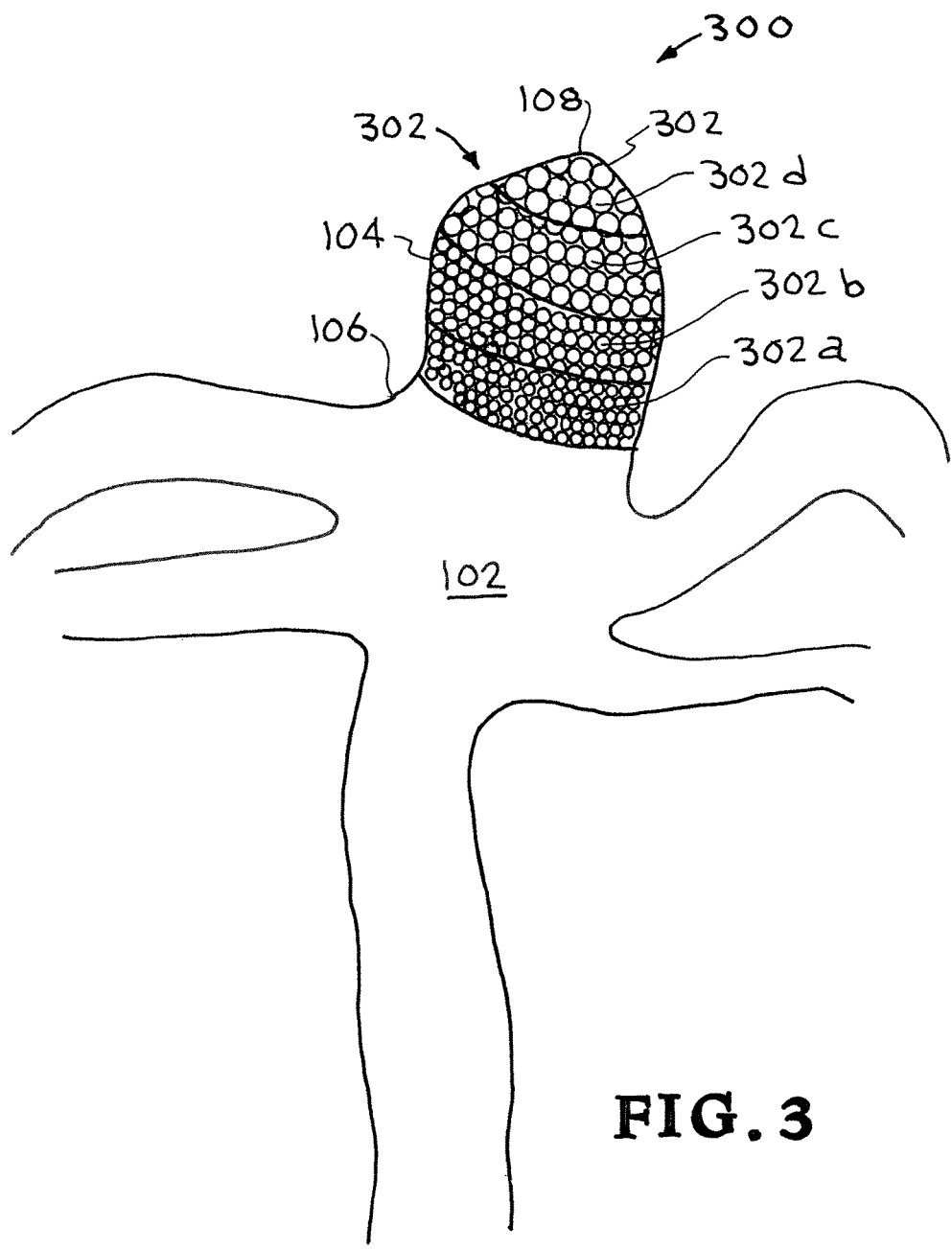
FIG. 3 is the illustration the blood vessel and artery system with an aneurysm shown in FIG. 1 wherein separate pieces of foam with differing pore sizes fill the aneurysm 104.

Referring now to FIG. 3, another embodiment of the present invention is illustrated. This embodiment is designated generally by the reference numeral 300. The illustration shows the blood vessel and artery system 102 and the aneurysm 104 that were shown in FIG. 1. The aneurysm 104 is shown with a dome 108 and a neck 106. As illustrated in FIG. 3, separate pieces of SMP foam unit 302 with differing pore sizes fill the aneurysm 104. The separate pieces of SMP foam unit 302 with differing pore sizes have a gradation of SMP foam pore size 302a, 302b, 302c, and 302d in a discrete fashion from one end of the SMP foam unit 302 to the other end. This places the least permeable portion 302a of the SMP foam nearest the parent artery, where the blood flow has the highest speed. Consequently, the small pore sizes 302a near the aneurysm neck rapidly decelerate the flow as it enters the aneurysm. Near the aneurysm fundus, where the blood flow has a much smaller speed, the pore sizes 302d are larger since it is not necessary to further decelerate the flow in this region. Through this gradation of pore sizes 302a, 302b, 302c, and 302d the total amount of polymer material comprising the device can be reduced.

Example 3

Coating Base of the SMP Foam

Figure 4:
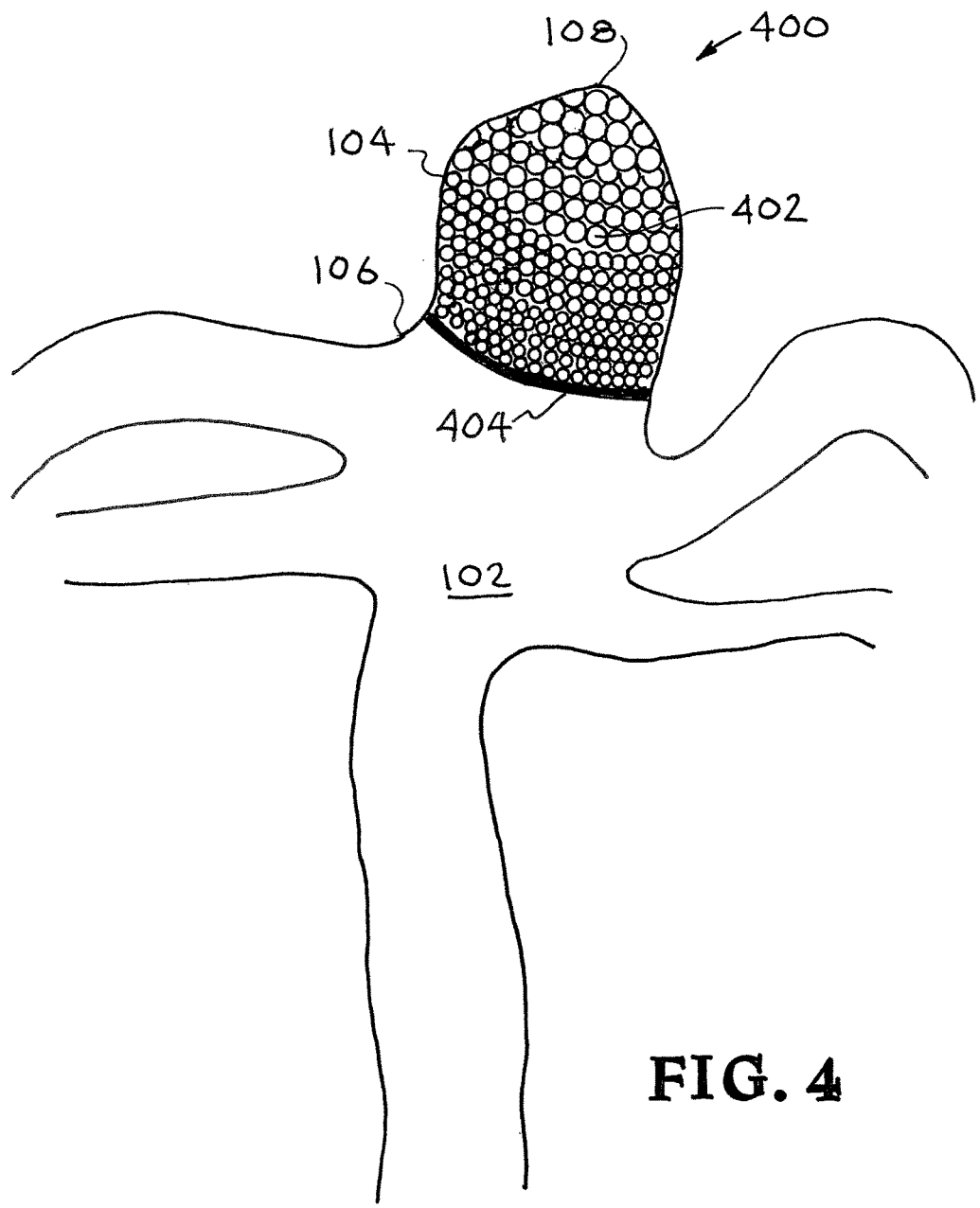
FIG. 4 is the illustration the blood vessel and artery system with an aneurysm shown in FIG. 1 wherein a foam unit fills the aneurysm and a layer of non-porous SMP coats the base of the foam unit.

Referring now to FIG. 4, another embodiment of the present invention is illustrated. This embodiment is designated generally by the reference numeral 400. The illustration shows the blood vessel and artery system 102 and the aneurysm 104 that were shown in FIG. 1. The aneurysm 104 is shown with a dome 108 and a neck 106. As illustrated in FIG. 4, a SMP foam unit 402 fills the aneurysm 104. A layer of non-porous SMP 404 coats the base of the SMP foam unit 402. This provides an impermeable layer that provides further enhancement of the hemodynamic conditions to promote thrombus formation. Consequently, the high speed parent artery flow cannot penetrate as deeply into the SMP foam and a greater portion of the blood within the treated aneurysm travels at a slower speed.

As illustrated in FIG. 4, the single piece of SMP foam 402 has a gradation of foam pore size in a continuous fashion from one end of the single piece of SMP foam to the other end. This places the least permeable portion of the SMP foam nearest the parent artery, where the blood flow has the highest speed. Consequently, the small pore sizes near the aneurysm neck rapidly decelerate the flow as it enters the aneurysm. Near the aneurysm fundus, where the blood flow has a much smaller speed, the pore sizes are larger since it is not necessary to further decelerate the flow in this region. Through this gradation of pore sizes, the total amount of polymer material comprising the device can be reduced.

Example 4

SMP Baffles within SMP Foam

Figure 5:
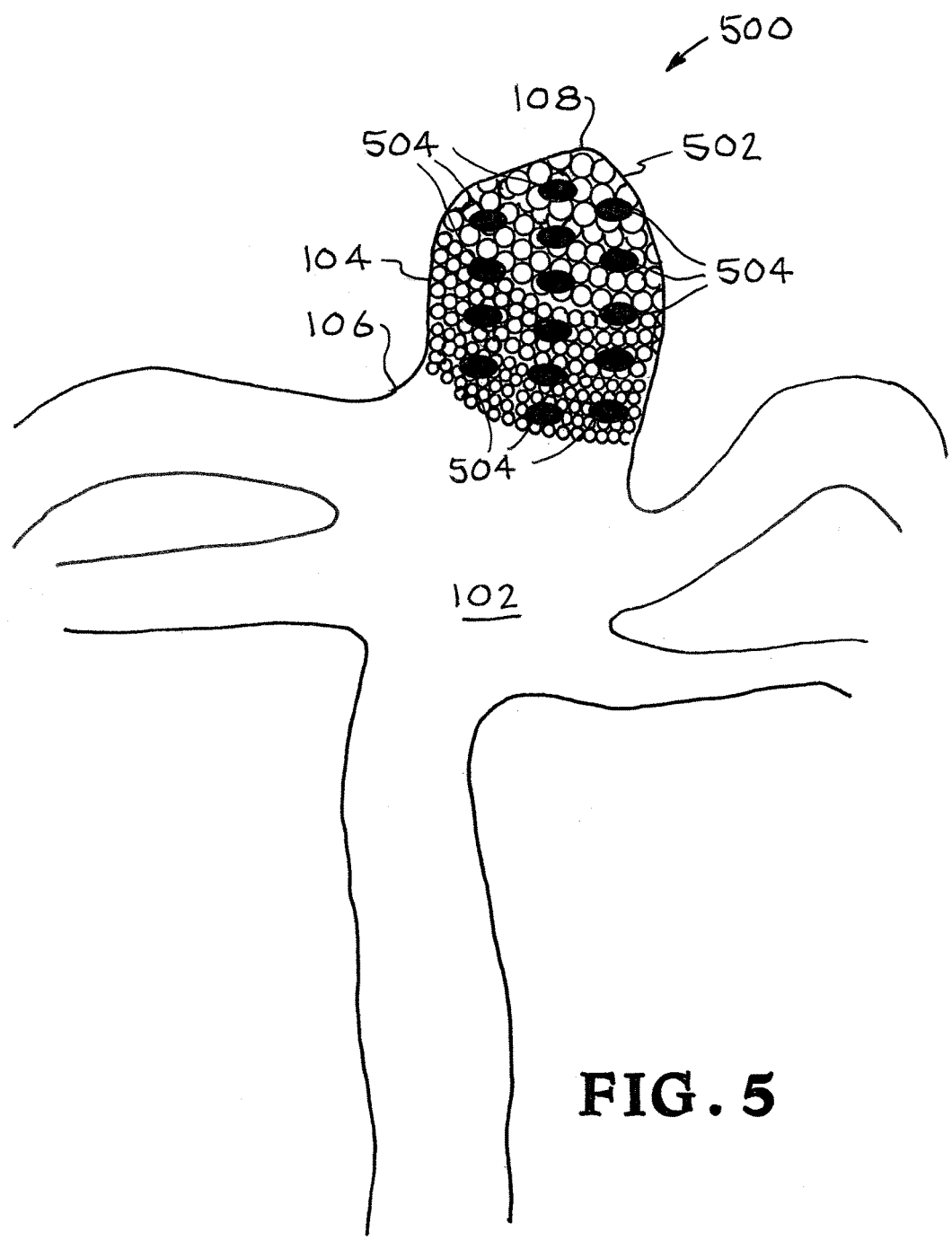
FIG. 5 is the illustration the blood vessel and artery system with an aneurysm shown in FIG. 1 wherein a piece of foam fills the aneurysm and an array of non-porous SMP baffles are distributed throughout the foam.

Referring now to FIG. 5, another embodiment of the present invention is illustrated. This embodiment is designated generally by the reference numeral 500. The illustration shows the blood vessel and artery system 102 and the aneurysm 104 that were shown in FIG. 1. The aneurysm 104 is shown with a dome 108 and a neck 106. As illustrated in FIG. 5, a SMP foam unit 502 fills the aneurysm 104. An array 504 of non-porous SMP baffles are distributed throughout the SMP foam unit 502. This provides impermeable baffles that provide further enhancement of the hemodynamic conditions that promote thrombus formation. Consequently, the high speed parent artery flow cannot penetrate as deeply into the SMP foam unit 502 and a greater portion of the blood within the treated aneurysm travels at a slower speed.

The SMP foam unit 502 has a gradation of foam pore size in a continuous fashion from one end of the single piece of SMP foam to the other end. This places the least permeable portion of the SMP foam nearest the parent artery, where the blood flow has the highest speed. Consequently, the small pore sizes near the aneurysm neck rapidly decelerate the flow as it enters the aneurysm. Near the aneurysm fundus, where the blood flow has a much smaller speed, the pore sizes are larger since it is not necessary to decelerate the flow in this region. Through this gradation of pore sizes, the total amount of polymer material comprising the device can be reduced.

Example 5

SMP Foam Pieces on Wire Backbone

Figure 6:
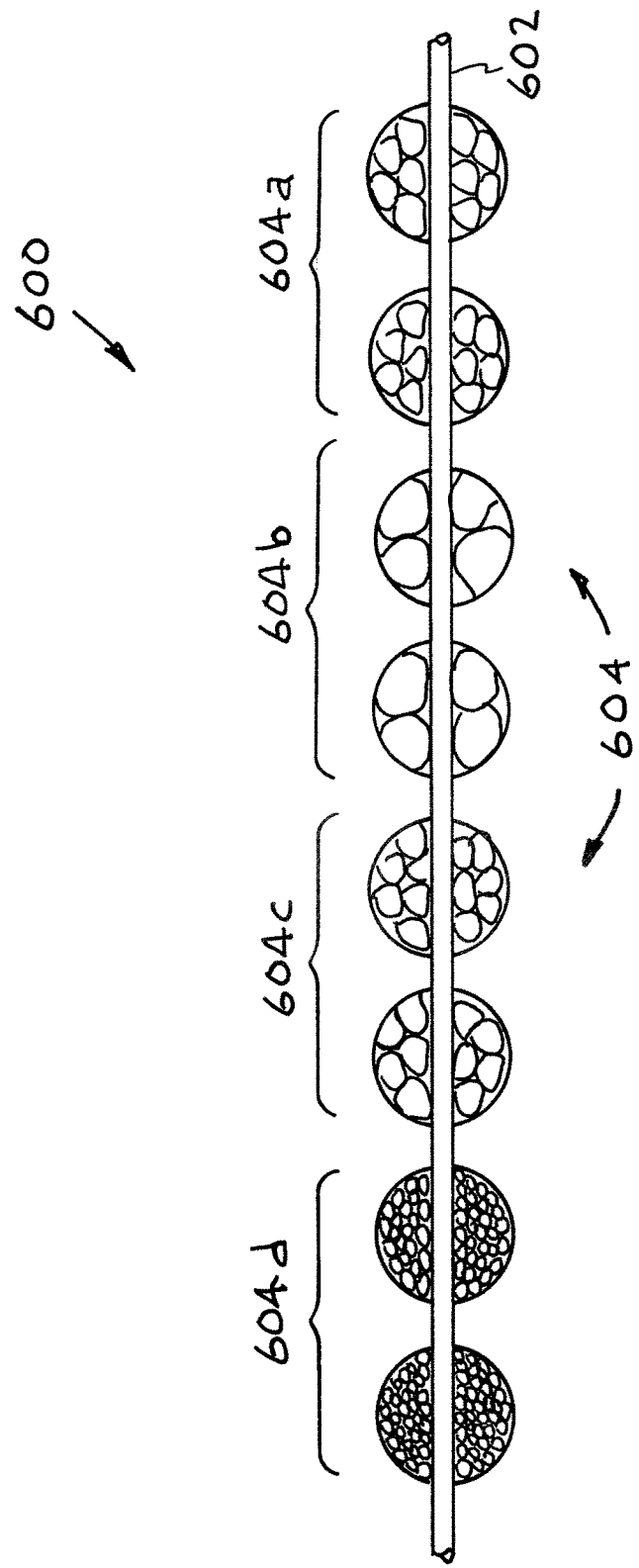
FIG. 6 illustrates a series of SMP foam pieces that are distributed along the wire backbone of a medical device.

Referring now to FIG. 6, another embodiment of the present invention is illustrated. This embodiment is designated generally by the reference numeral 600. In the embodiment 600, gradation of pore sizes is achieved through a series of SMP foam pieces 604 that are distributed along the wire backbone 602 of the medical device. The separate pieces of SMP foam have differing pore sizes 604a, 604b, 604c, and 604d in a discrete fashion from one end of the wire backbone 602 to the other end. The wire backbone 602 assumes a three-dimensional shape inside the aneurysm.

Figure 7:
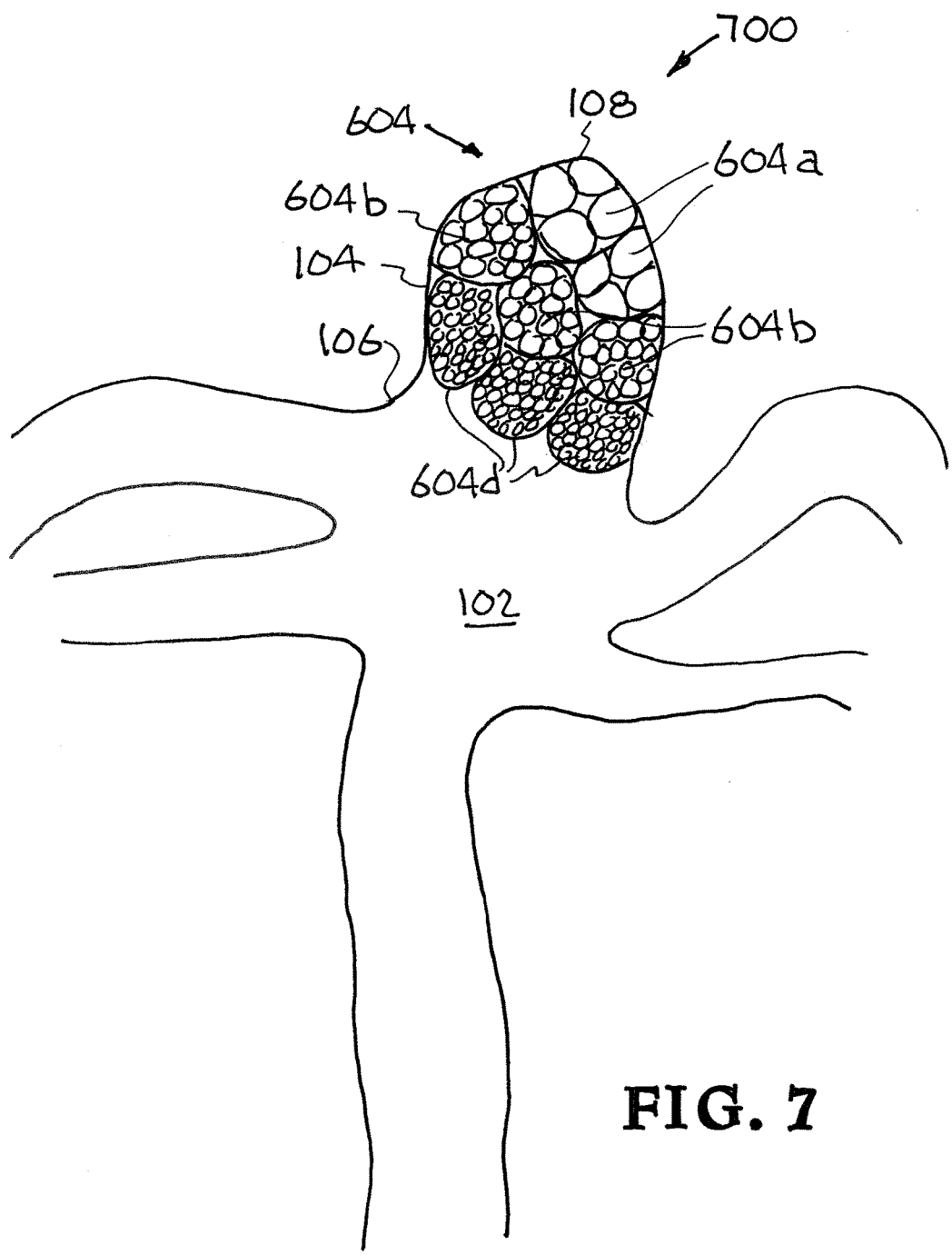
FIG. 7 illustrates the placement of the series of SMP foam pieces shown in FIG. 6 in the aneurysm.

Referring now to FIG. 7, the placement of the series of SMP foam pieces 604 in the aneurysm 104 is illustrated. The wire backbone 602 assumes a three-dimensional shape inside the aneurysm. As the wire backbone 602 with SMP foam pieces 604 is delivered to the aneurysm 104, the coiling action of the wire positions the various SMP foam pieces 604a, 604b, 604c, and 604d in such a manner as to place the pieces with the smallest pore sizes closest to the aneurysm neck 106. Consequently, the small pore sizes 604a near the aneurysm neck rapidly decelerate the flow as it enters the aneurysm. Near the aneurysm fundus, where the blood flow has a much smaller speed, the pore sizes 604b are larger since it is not necessary to decelerate the flow in this region. Through this gradation of pore sizes 604a, 604b, 604c, and 604d the total amount of polymer material comprising the device can be reduced.

Example 6

Single Monolithic SMP Foam on Wire Backbone

Figure 8:
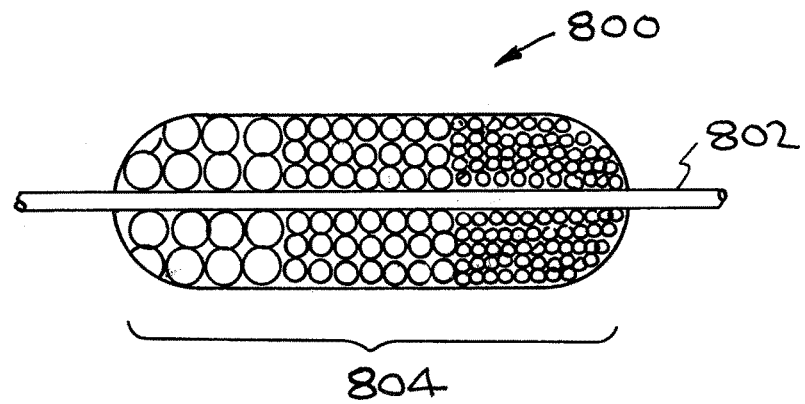
FIG. 8 illustrates a single monolithic SMP foam distributed along the wire backbone of a medical device.

Referring now to FIG. 8, another embodiment of the present invention is illustrated. This embodiment is designated generally by the reference numeral 800. In the embodiment 800, gradation of pore sizes is achieved through a single monolithic SMP foam 804 on wire backbone 802 of the medical device. The sections of the monolithic SMP foam have differing pore sizes 804 in a continuous fashion from one end of the wire backbone 802 to the other end. The wire backbone 802 assumes a three-dimensional shape inside the aneurysm.

Figure 9A:
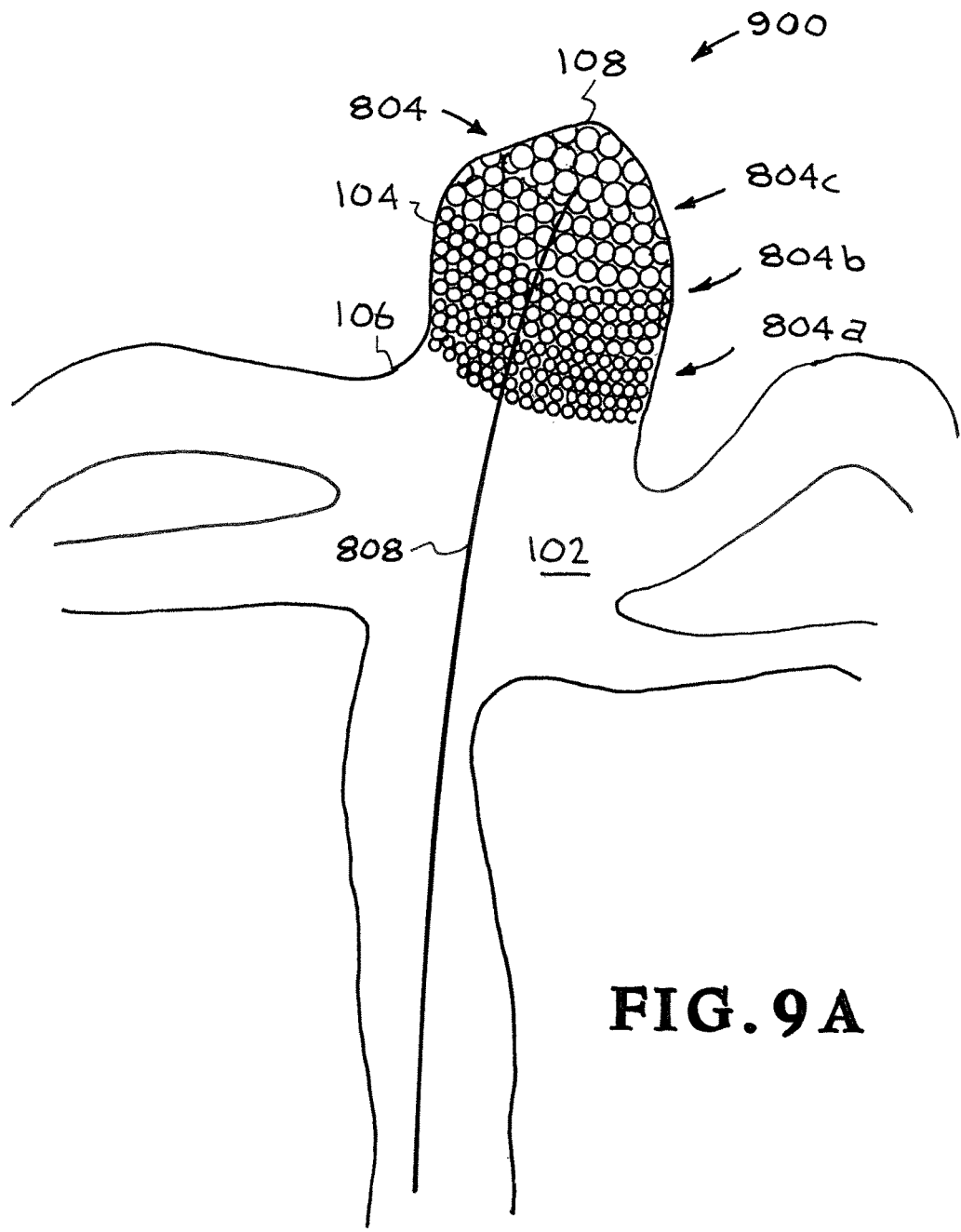
FIGS. 9A and 9B illustrate the placement of the single monolithic SMP foam shown in FIG. 8 in the aneurysm.
Figure 9B:
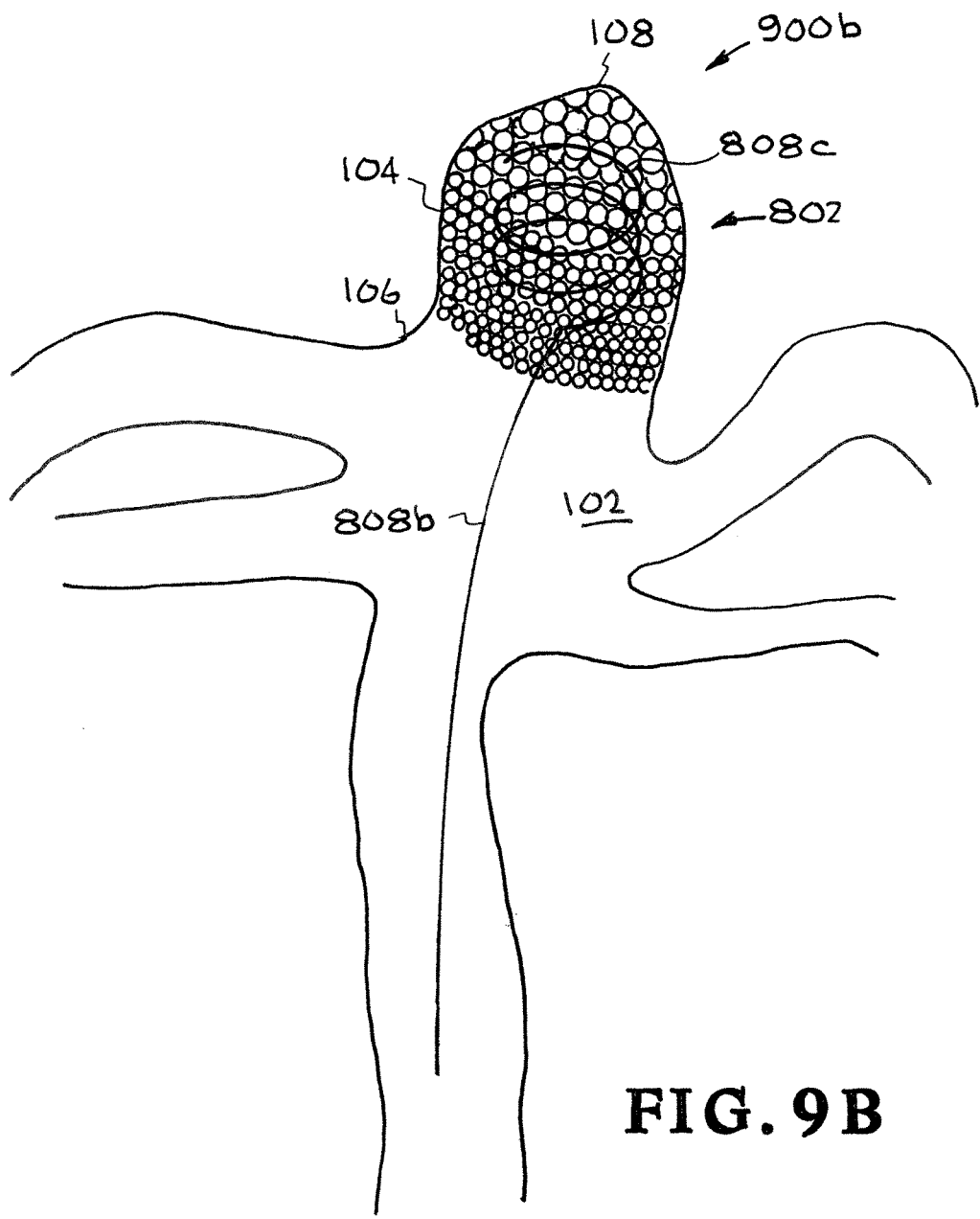

Referring now to FIGS. 9A and 9B, the placement of the single monolithic SMP foam 804 in the aneurysm 104 is illustrated. The single monolithic SMP foam 804 and the wire backbone 802 are positioned with a guidewire 808. The guidewire 808 shown in FIG. 9A is removed. The guidewire 808b shown in FIG. 9B is also removed; however, the wire 808c remains in the aneurysm 104. The wire backbone 802 assumes a three-dimensional shape inside the aneurysm. As the wire backbone 802 with single monolithic SMP foam 804 is delivered to the aneurysm 104, the coiling action of the wire 808c positions the monolithic SMP foam sections 804a, 804b, and 804c in such a manner as to place the section with the smallest pore sizes closest to the aneurysm neck 106. Consequently, the small pore sizes 804a near the aneurysm neck rapidly decelerate the flow as it enters the aneurysm. Near the aneurysm fundus, where the blood flow has a much smaller speed, the pore sizes 804c are larger since it is not necessary to decelerate the flow in this region. Through this gradation of pore sizes 804a, 804b, and 804c the total amount of polymer material comprising the device can be reduced.

Example 7

Fusiform Aneurysm

Figure 10:
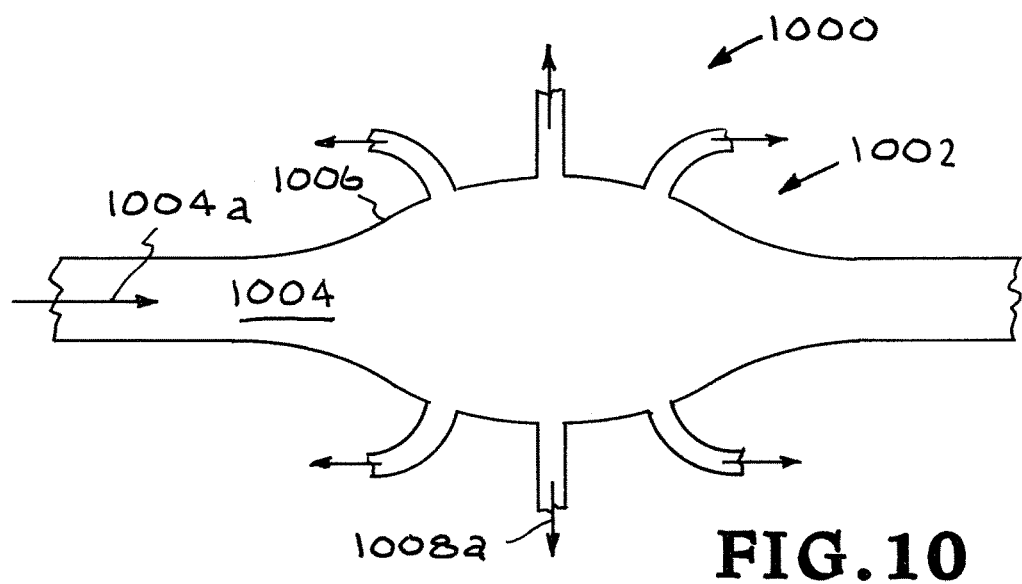
FIG. 10 is an illustration showing a blood vessel and artery system with a fusiform aneurysm.

Referring now to FIG. 10, an illustration of a fusiform aneurysm is provided. The illustration is designated generally by the reference numeral 1000. The illustration 1000 shows a fusiform aneurysm 1002 that is a bulging or ballooning in the wall 1006 of the parent artery 1004. Parent artery flow is represented by the arrow 1004a. Blood vessels 1008 extend from the parent artery 1004. Blood vessel flow is represented by the arrow 1008a.

Figure 11:
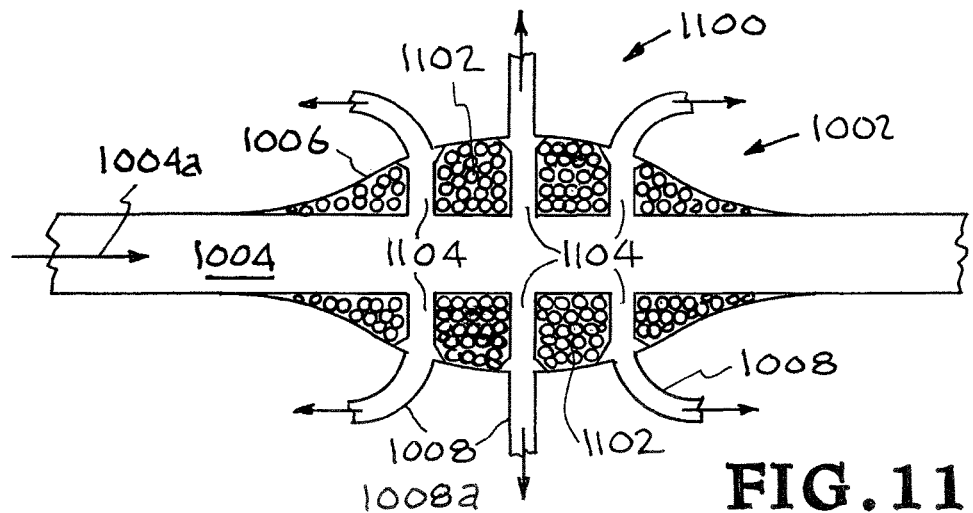
FIG. 11 is an illustration showing the fusiform aneurysm that was illustrated in FIG. 10 filled with a SMP foam device.

Referring now to FIG. 11, an illustration shows the fusiform aneurysm 1002 that was illustrated in FIG. 10 filled with a SMP foam device 1102. The illustration of the fusiform aneurysm 1002 filled with a SMP foam device 1102 is designated generally by the reference numeral 1100. The illustration 1100 shows the fusiform aneurysm 1002 filled with the SMP foam device 1102 with internal channels 1104 to transfer blood flow from the parent artery 1004 to the blood vessels 1008 arising from the aneurysm wall 1006. The SMP foam 1102 fills the bulging portion of the fusiform aneurysm 1002.

Example 8

Fusiform Aneurysm SMP Foam Device with Dimples

Figure 12:
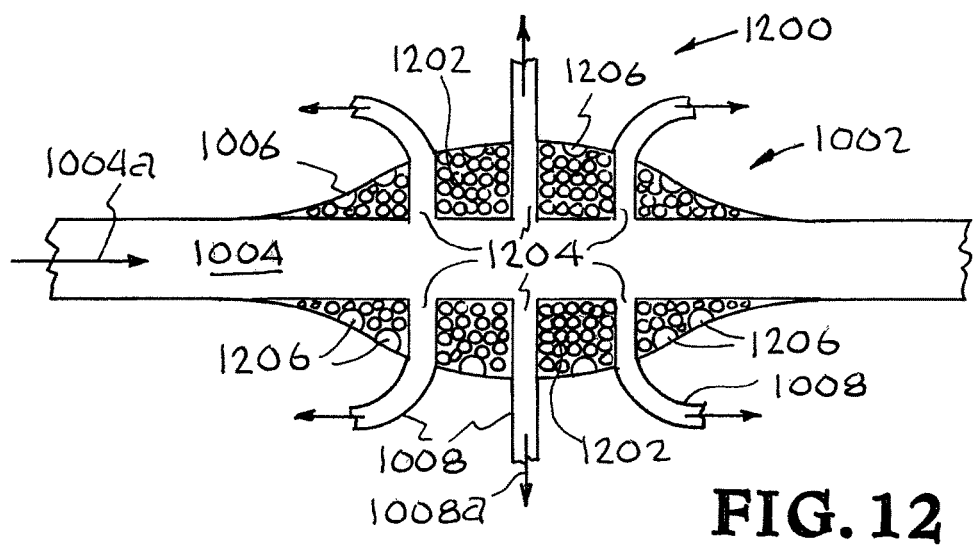
FIG. 12 is an illustration shows the fusiform aneurysm that was illustrated in FIG. 10 filled with a SMP foam device.

Referring now to FIG. 12, an illustration shows the fusiform aneurysm 1002 that was illustrated in FIG. 10 filled with a SMP foam device 1202. The illustration of the fusiform aneurysm 1002 filled with a SMP foam device 1202 is designated generally by the reference numeral 1200. The illustration 1200 shows the fusiform aneurysm 1002 filled with the SMP foam device 1202 with internal channels 1204 to transfer blood flow from the parent artery 1004 to the blood vessels 1008 arising from the aneurysm wall 1006. The SMP foam 1202 fills the bulging portion of the aneurysm 1002. The external dimples 1206 promote a healing response to the treatment procedure.

Figure 13:
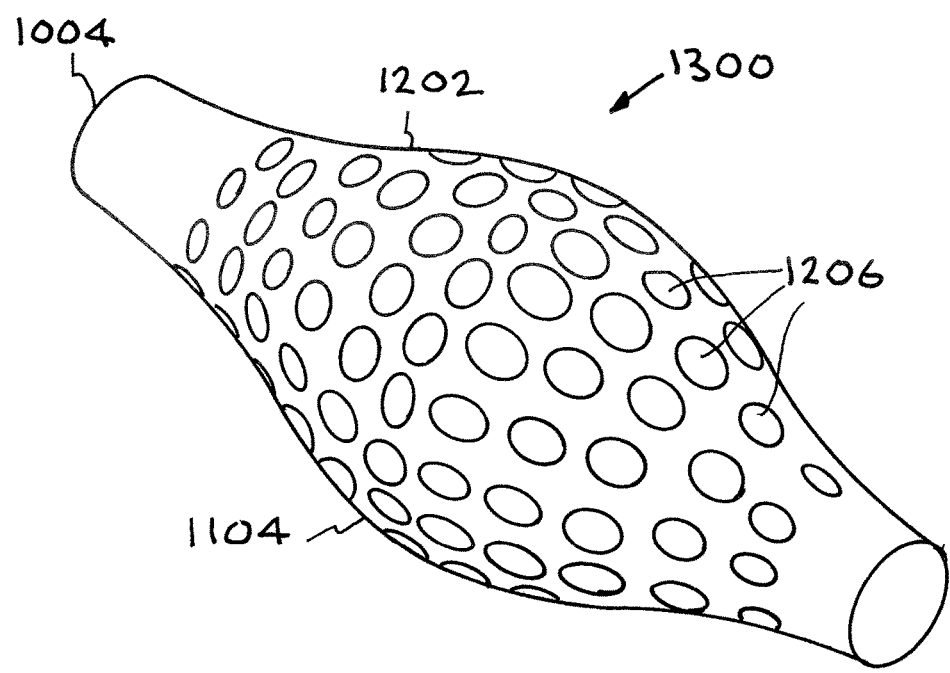
FIG. 13 is an illustration shows the fusiform aneurysm that was illustrated in FIG. 10 and having dimples on the exterior.

Referring now to FIG. 13, an illustration shows the SMP foam device 1002 having the internal channels to transfer blood flow from the parent artery to the blood vessels. The SMP foam fills the bulging portion 1300 of the aneurysm 1002. The external dimples 1206 promote a healing response to the treatment procedure.

Example 9

Void at Dome

Figure 14:
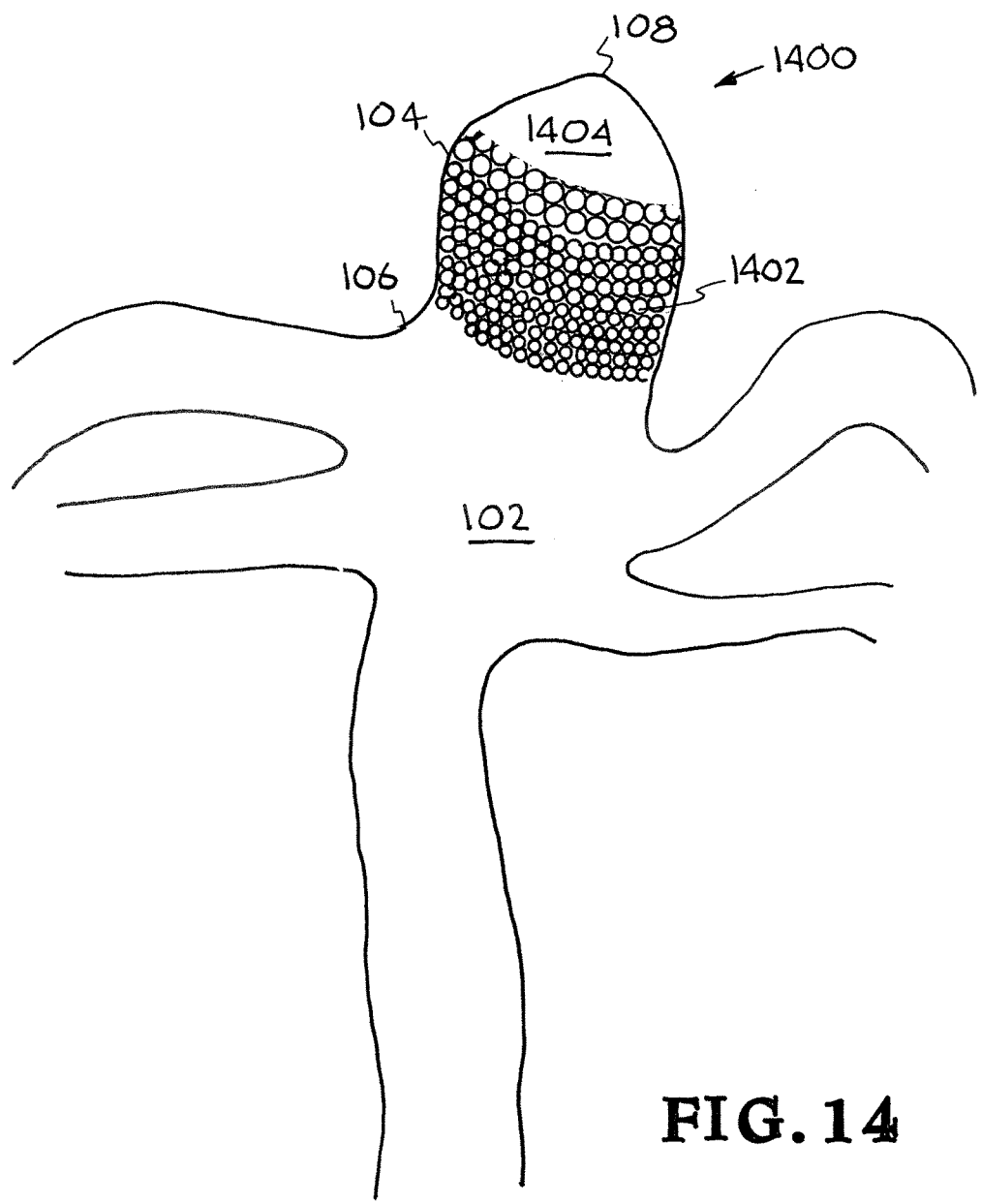
FIG. 14 is the illustration the blood vessel and artery system with an aneurysm shown in FIG. 1 wherein a foam unit fills the neck and a portion of the interior of the aneurysm but leaves a void in the dome of the aneurysm.

Referring now to FIG. 14, an illustration shows the blood vessel and artery system and the aneurysm that were illustrated in FIG. 1 with an embodiment of the invention including a void at the dome. The illustration is designated generally by the reference numeral 1400. The illustration 1400 shows the cerebral arteries and blood vessels 102 and the aneurysm 104. The aneurysm 104 is shown with a dome 108 and a neck 106. The aneurysm 104 is shown with a piece of SMP foam 1402 in the aneurysm 104 partially filling the aneurysm 104. The upper portion of the aneurysm 104 is a void 1404. The SMP foam may not be necessary in the void 1404 in the upper portion of the aneurysm 104.

Example 10

Void at Dome and Impermeable Layer at Neck

Figure 15:
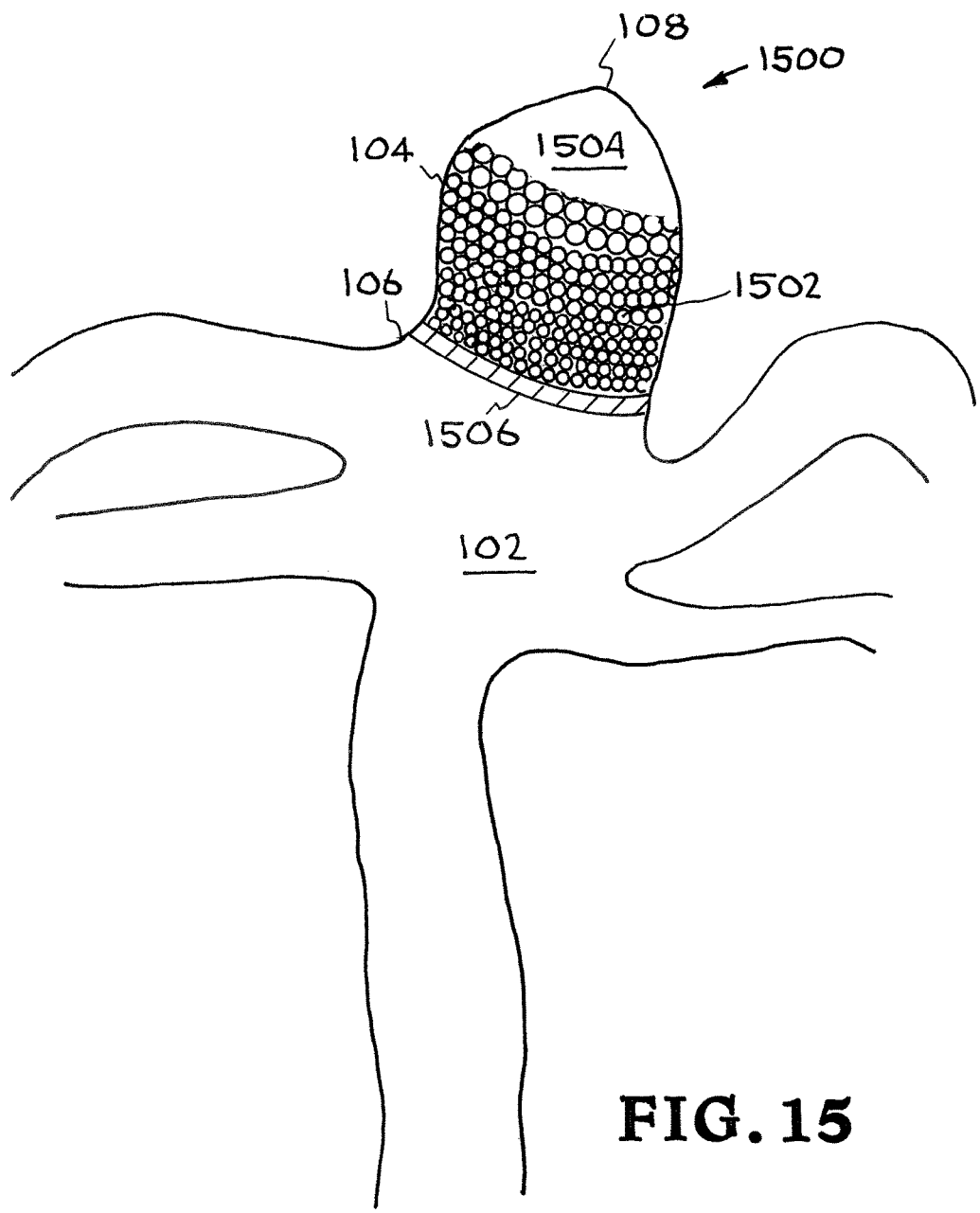
FIG. 15 is the illustration the blood vessel and artery system with an aneurysm shown in FIG. 1 wherein a foam unit fills the neck and a portion of the interior of the aneurysm but leaves a void in the dome of the aneurysm and including an impermeable layer in the neck.

Referring now to FIG. 15, an illustration shows the blood vessel and artery system and the aneurysm that were illustrated in FIG. 1 with an embodiment of the invention including a void at the dome and an impermeable layer at the neck. The illustration is designated generally by the reference numeral 1500. The illustration 1500 shows the cerebral arteries and blood vessels 102 and the aneurysm 104. The aneurysm 104 is shown with a dome 108 and a neck 106. The aneurysm 104 is shown with a piece of SMP foam 1502 in the aneurysm 104 partially filling the aneurysm 104. The upper portion of the aneurysm 104 is a void 1504. The SMP foam may not be necessary in the void 1504 in the upper portion of the aneurysm 104. A layer of non-porous SMP 1506 coats the base of the SMP foam unit 1502. This provides an impermeable layer that provides further enhancement of the hemodynamic conditions that promote thrombus formation and subsequent healing. Consequently, the high speed parent artery flow cannot penetrate as deeply into the SMP foam and a greater portion of the blood within the treated aneurysm travels at a slower speed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus to treat an aneurysm in a blood vessel, wherein the aneurysm has a dome, an interior, and a neck; comprising:
   a shape memory polymer foam to be boated in the interior of the aneurysm between the dome and the neck; and
   at least one fluid transport channel that includes: a first portion in a first peripheral wall of the shape memory polymer foam, a second portion in a second peripheral wall of the shape memory polymer foam, and a third portion that couples the first and second portions to each other;
   wherein said shape memory polymer foam has pores that include a first multiplicity of pores having a first pore size and a second multiplicity of pores having a second pore size, said second pore size being larger than said first pore size;
   wherein said first multiplicity of pores having a first pore size are configured to be located in the neck of the aneurysm;
   wherein the third portion includes at least one of the first and second multiplicities of pores.

2. The apparatus of claim 1 wherein said second multiplicity of pores having a second pore size are configured to be located in the dome of the aneurysm.

3. The apparatus of claim 1 further comprising additional multiplicities of pores in said shape memory polymer foam, wherein said additional multiplicities of pores have pore sizes larger than said first pore size but smaller than said second pore size.

4. The apparatus of claim 3 wherein said first multiplicity of pores, said additional multiplicities of pores, and said second multiplicity of pores are configured to be located in the interior of the aneurysm with a gradation of pore size wherein the pores with the smallest pore size are configured to be in the neck of the aneurysm and the pores with the largest pore size are configured to be in the dome of the aneurysm.

5. The apparatus of claim 1 wherein said shape memory polymer foam comprises separate pieces of shape memory polymer foam with differing pore sizes to be located in the interior of the aneurysm between the dome and the neck.

6. The apparatus of claim 5 wherein the separate pieces of shape memory polymer foam are not monolithic with each other.

7. The apparatus of claim 1 wherein said shape memory polymer foam comprises a shape memory polymer foam unit with differing pore sizes to be located in the interior of the aneurysm between the dome and the neck, said shape memory polymer foam unit having a base configured to be located in the neck of the aneurysm, and further comprising a coating of non-porous shape memory polymer on said base of the foam unit.

8. The apparatus of claim 1 further comprising an array of non-porous baffles in said shape memory polymer foam to be located in the interior of the aneurysm between the dome and the neck; wherein the baffles are located between walls of the shape memory polymer foam.

9. The apparatus of claim 1 further comprising a wire backbone, wherein said shape memory polymer foam comprises a series of shape memory polymer foam pieces that are distributed along said wire backbone.

10. The apparatus of claim 1 further comprising a wire backbone, wherein said shape memory polymer foam comprises a single monolithic shape memory polymer foam unit located on said wire backbone.

11. The apparatus of claim 1 wherein said shape memory polymer foam comprises a shape memory polymer foam unit with differing pore sizes to be located in the interior of the aneurysm between the dome and the neck, said shape memory polymer foam unit having a base configured to be located in the neck of the aneurysm, further comprising a coating of non-porous shape memory polymer on said base of the foam unit and further comprising a void in the interior of the aneurysm, wherein said void is located in the dome of the aneurysm.

12. The apparatus of claim 1, wherein:
a single axis intersects the second multiplicity of pores, the first and second peripheral walls of the shape memory polymer foam, and a middle portion of the shape memory polymer foam that couples the first and second peripheral walls to each other; and
the second multiplicity of pores extend from the first peripheral wall all the way through the middle portion of the shape memory polymer and all the way to the second peripheral wall.

13. The apparatus of claim 1 wherein the shape memory polymer foam has a peripheral wall that includes dimples.

* * * * *

UNITED STATES PATENT AND TRADEMARK OFFICE
CERTIFICATE OF CORRECTION

Page 1 of 1

PATENT NO. : 9,662,119 B2
APPLICATION NO. : 13/798740
DATED : May 30, 2017
INVENTOR(S) : Jason M. Ortega et al.

It is certified that error appears in the above-identified patent and that said Letters Patent is hereby corrected as shown below:

In the Claims

Column 10:
Line 19, --boated-- should read "located".

Signed and Sealed this
Twenty-first Day of July, 2020

Andrei Iancu
*Director of the United States Patent and Trademark Office*